Figure 1:
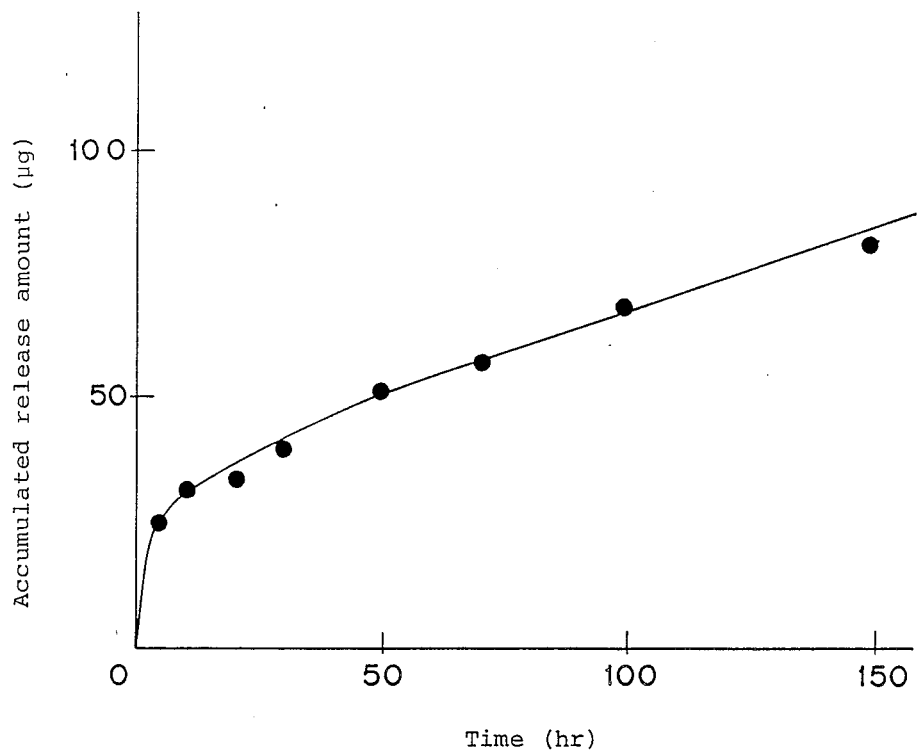

United States Patent [19]

Fujioka et al.

[11] Patent Number: 4,985,253

[45] Date of Patent: Jan. 15, 1991

[54] SUSTAINED RELEASE COMPOSITION FOR PHARMACEUTICAL SUBSTANCES COMPRISING A SILICONE ELASTOMER CARRIER

[75] Inventors: Keiji Fujioka, Amagasaki; Shigeji Sato, Ibaraki; Nobuhiko Tamura, Toyonaka; Yoshihiro Takada, Takatsuki, all of Japan

[73] Assignee: Sumitomo Pharmaceuticals Company, Limited, Osaka, Japan

[21] Appl. No.: 481,722

[22] Filed: Feb. 16, 1990

Related U.S. Application Data

[63] Continuation of Ser. No. 917,471, Oct. 10, 1986, abandoned.

[30] Foreign Application Priority Data

| Oct. 11, 1985 | [JP] | Japan | 60-227590 |
| Sep. 19, 1986 | [JP] | Japan | 61-223250 |
| Sep. 19, 1986 | [JP] | Japan | 61-223251 |

[51] Int. Cl.$^5$ .................. A61K 9/14; A61F 13/00
[52] U.S. Cl. .................. 424/488; 424/422
[58] Field of Search .................. 424/422–426, 424/430–433, 474–433, 474–483, 484, 488; 604/822, 890.1–890.3, DIG. 21; 530/362–369; 128/DIG. 21

[56] References Cited

U.S. PATENT DOCUMENTS

| 3,279,996 | 10/1966 | Long et al. | 424/424 |
| 3,545,439 | 12/1970 | Duncan | 424/432 |
| 4,004,979 | 1/1977 | Avrameas et al. | 538/812 |
| 4,012,497 | 3/1977 | Schopflin | 424/432 |
| 4,053,580 | 10/1977 | Chien et al. | 424/425 |
| 4,164,560 | 8/1979 | Folkman et al. | 424/422 |
| 4,191,741 | 3/1980 | Hudson et al. | |
| 4,230,686 | 10/1980 | Schopflin et al. | 424/425 |
| 4,275,000 | 6/1981 | Ross | 530/363 |
| 4,357,312 | 11/1982 | Hseih et al. | 424/425 |
| 4,376,765 | 3/1983 | Trouet et al. | 514/18 |
| 4,391,797 | 7/1983 | Folkman et al. | 424/425 |
| 4,452,775 | 6/1984 | Kent | 424/425 |
| 4,464,468 | 8/1984 | Avrameas et al. | 530/362 |
| 4,478,596 | 10/1984 | Michelson | 604/890 |
| 4,559,054 | 12/1985 | Bruck | 604/892 |
| 4,591,496 | 5/1986 | Cohen et al. | 424/467 |
| 4,613,330 | 9/1986 | Michelson | 604/890 |
| 4,650,772 | 3/1987 | Dodge et al. | 530/367 |

FOREIGN PATENT DOCUMENTS

| 0139286 | 5/1985 | European Pat. Off. . |
| 0152736 | 8/1985 | European Pat. Off. . |
| 2021412 | 12/1979 | United Kingdom . |

OTHER PUBLICATIONS

The Merck Index, 10th Ed., 1983, pp. 33, 723, 724.
Il Farmaco Edizione Pratica, pp. 377–389, vol. 37 (1982).
Journal of Pharmacy and Pharmacology, vol. 31, No. 9, pp. 649–650 (Sep. 1979).
Pharmaceutical Technology, vol. 9, No. 6, pp. 39, 40, 42, 46, 48, 49 (Jun. 1985).
In Vitro, vol. 19, No. 10, pp. 743–748 (Oct. 1983).

Primary Examiner—C. Fred Rosenbaum
Assistant Examiner—Sharon Rose
Attorney, Agent, or Firm—Birch, Stewart, Kolasch & Birch

[57] ABSTRACT

A sustained release composition applicable for human beings and mammals which comprises (a) a silicone elastomer and (b) a pharmaceutical substance optionally with (c) albumin. When the pharmaceutical substance is of high molecular weight, and can exert its pharmaceutical effect in a trace amount, its continuous release over a long period is attained by application of this invention.

24 Claims, 4 Drawing Sheets

SUSTAINED RELEASE COMPOSITION FOR PHARMACEUTICAL SUBSTANCES COMPRISING A SILICONE ELASTOMER CARRIER

This application is a continuation of application Ser. No. 06/917,471 filed on Oct. 10, 1986, now abandoned.

The present invention relates to a sustained release composition. More particularly, it relates to a long-term sustained release composition to be applied to mammals or human beings which comprises a pharmaceutical (i.e. pharmacologically or physiologically active) substance, particularly of high molecular weight, as an active ingredient and which can maintain an effective level of said pharmaceutical substance over a long period of time.

Silicone elastomers are said to release pharmaceutical substances contained therein only by diffusion and are considered to assure desirable release rates of pharmaceutical substances over a long period of time. It is, however, reported that only low molecular weight hydrophobic substances having molecular weights of 600 to 1,000 can pass through the matrixes of silicone elastomers, and in fact, the pharmaceutical substances usable in such sustained release compositions comprising silicone elastomers as the carrier were restricted to hydrophobic low molecular weight ones such as progesterone, estradiol and nitroglycerine (Japanese Patent Publication (unexamined) Nos. 45694/80 and 59806/82). Thus, silicone elastomers were considered not to be favorable carriers for hydrophilic low molecular weight pharmaceutical substances as well as high molecular weight pharmaceutical substances.

Recently, Dean Hsieh et al reported the successful sustained release of such high molecular weight pharmaceutical substances as bovine serum albumin (BSA), chymotrypsin, etc. from silicone elastomers by the use of water soluble mixing agents (e.g. polyethylene glycol 400, sodium chloride) or oily plasticizers (e.g. polydimethylsiloxane liquid), which has heretofore been adopted for increasing the permeability of hydrophobic low molecular weight substances (Pharmaceutical Technology, pages 39–49 (1985)). However, the content of high molecular weight pharmaceutical substances in silicone elastomers are required to be as high as 20 to 50 % by weight, and a low content such as 20 % can not assure good subtained release. When the high molecular weight pharmaceutical substances are readily available, such as BSA or chymotrypsin, the need for such high contents is not problematic. However, for substance which are hardly available, such as interferon or growth hormone, the inclusion of a high context is practically difficult. Further, since various proteins exert their pharmacological or physical activity in trace or very small amounts, their inclusion in high contents is rather unfavorable. Even when appropriate amounts suitable for the purpose of application are included in silicone elastomers, desirable sustained release can be hardly achieved in case of the inclusion in trace amounts, since the release rates of pharmaceutical sustances from silicone elastomers are theoretically proportional to the square root of the initial contents of said pharamceutical substances. In addition, most proteins exerting their pharmacological or physiological activity in trace or very small amounts are relatively unstable, and their stabilization over a long period of time is essential for their use in sustained release compositions This has not successfully been achieved in conventional preparations.

Aiming at achievement of a desirable release of a high molecular weight pharmaceutical substance which is to be administered in a trace or very small amount continuously over a long period of time, an extensive study has been carried out, and as a result, it has been found that the use of a silicone elastomer is suitable for such aim. It has also been found that even when the content of a high molecular weight pharmaceutical substance in a silicone elastomer is small, good release can be attained. It has further been found that albumin can assure good sustained release of any pharmaceutical substance from a silicone elastomer and simultaneously attain stabilization of said pharmaceutical substance in the silicone elastomer.

According to this invention, there is provided a sustained release composition comprising a silicone elastomer as a carrier and a high molecular weight pharmaceutical substance, particularly desired to be administered in a trace or very small amount continuosuly over a long period of time, contained therein in a relatively low content. There is also provided a sustained release composition comprising a silicone elastomer as a carrier and a pharmaceutical substance, desired to administer continuosuly over a long period of time, and albumin.

The silicone elastomer is an elastomer consisting of a silicone polymer such as methylpolysiloxane, dimethylpolysiloxane or dimethylmethylvinylpolysiloxane, and there may be used any pharmacologically or physiologically acceptable silicone elastomer. Taking the easiness of handling, the stability to heat, etc. into consideration, the use of a silicone polymer curable at room temperature is favorable. This silicone elastomer as a liquid elastomer base is cured by addition of a curing agent (e.g. stannous octate, chloroplatinic acid) thereto to give a solid rubber. Particularly preferred examples of the silicone polymer are dimethylpolysiloxane of the formula:

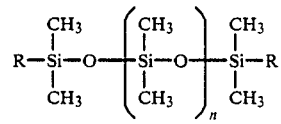

wherein n is a numeral of 100 to 5,000 and R is methyl, hydroxyl or vinyl (e.g. "Dow Corning 360", "Silastic 382", "Dow Corning MDX-4-4210"), methylvinylpolysiloxane of the formula:

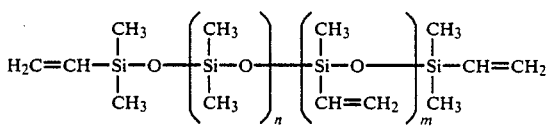

wherein n is a numeral of 100 to 10,000 and m is a numeral of 1 to 100 (e.g. "Silastic Medical Grade ETR"), etc.

The pharmaceutical substance may be any pharmacologically or physiologically active substance applicable to mammals or human beings In general, however, the one having a high molecular weight of about 1,000 to 500,000 chosen from peptides, proteins, sugar proteins, polysaccharides, etc. is preferred. Especially suitable are high molecular weight pharmaceutical substances, which have strong pharmacological or physiological activity and are desired to be administered in trace or very small amounts continuously over a long period of time. Examples of such pharmaceutical substances are those having growth regulating activity, bone metabolizing activity, thrombolytic activity, immunoregulating activity, etc.

Pharmaceutical substances having growth regulating activity are growth hormone (GH), growth hormone releasing factor (GRF), somatomedin (SM), etc. GFR includes peptides showing GH releasing activity, and there are known several kinds of peptides, i.e. those having 44, 40, 37 or 29 amino acids. SM covers SM-A, SM-B, SM-C, insulin-like growth factor I (IGF-I), IGF-II, multiplication stimulating activity (MSA), etc. A typical example of those having bone metabolizing activity is calcitonin, and a typical example of those having thrombolytic activity is tissue plasminogen activator (TPA). Examples of pharmaceutical substances having immunoregulating activity are interferon (IFN), interleukin (IL), colony stimulating factor (CSF), macrophage activating factor (MAF), macrophage migration inhibitory factor (MIF), etc. Interferon may be any one chosen from alpha, beta, gamma and so or. Likewise, interleukin may be any one chosen from IL-1, IL-2, IL-3, etc. CSF may be multi-CSF, GM-CSF, G-CSF, M-CSF or the like. These may be obtained by extraction from natural sources, e.g. living bodies, by artificial synthesis, by genetic engineering, etc. These may be employed alone or in combination.

When albumin is used as an essential component, the pharmaceutical substance may be of low molecular weight. Examples of such pharmaceutical substance are anti-inflammatory substances (e.g. indomethacin, flurbiprofen, ketoprofen, ibuprofen, phenylbutazone), antibiotics (e.g. beta-lactams, aminoglycosides, macrolides, tetracyclines, pyridonecarboxylic acids, phosphomycin), anti-tumor agents (e.g. adriamycin, cisplatin, bleomycin, mitomycin, fluorouracil, vinblastine, vincristine), amino acids (e.g. ascorbic acid, N-acetyltryptophan), antifungal agents, prostaglandins, vitamins, steroids, etc.

As the albumin, there may be used ovalbumin, lactalbumin, serum albumin, etc. From the viewpoints of releasing effect and stabilization effect, the use of serum albumin such as human serum albumin or bovine serum albumin is preferred. When the sustained release composition is to be applied to human beings, the use of human serum albumin is particularly preferred. Likewise, the use of bovine serum albumin is especially preferred for application to cows.

The release rate of the pharmaceutical substance from the silicone elastomer can be controlled by incorporating a water-soluble or fat-soluble mixing agent or cosolvent (e.g. polyethylene glycol 400, polyethylene glycol 200. ethylene glycol, glycerol, polysorbate 80, sodium alginate, L-alanine, sodium chloride, polydimethylsiloxane) into the silicone elastomer. Any other additive may be also incorporated into the silicone elastomer for the purpose of accelerating the release rate.

In the sustained release composition of the invention, the content of the pharmaceutical substance may be appropriately controlled depending upon the dose to be administered, the extent of sustaining, the release rate, etc. Usually and particularly when the composition is shaped in a matrix type preparation, the content of the pharmaceutical substance may be usually from 5 to 40 % by weight, and in this invention, good sustained release can be observed even at a content of not more than 15 % by weight, for instance, 9 % by weight or less. When, for instance, the pharmaceutical substance is GRF, good sustained release is assured even at a content of about 6 to 10 % by weight.

When albumin is used as an essential component, the content of the pharmaceutical substance in the sustained release composition may be usually not more than 50 % by weight, preferably from 1 to 20 % by weight. Albumin is normally employed in a content of not more than 50 % by weight, preferably from 20 to 30 % by weight. The silicone elastomer may be contained in an amount of not less than 50 % by weight, preferably from 70 to 90 % by weight.

Irrespective of whether albumin is used or not, the curing agent may be employed in an amount of not more than 15 % by weight, preferably 1 to 10 % by weight on the basis of the total weight of the composition. The additives such as plasticizers may be used in an amount of not more than 45 % by weight, preferably from 1 to 20 % by weight.

For preparation of the subtained release composition of the invention, said essential components may be mixed together in any optional order. When albumin is used as the essential component, the pharmaceutical substance and albumin are usually combined first to make their mixture, preferably in a solid state. For instance, the pharmaceutical substance in a powder state and albumin in a powder state are mixed together in an appropriate proportion to make a solid mixture. Further, for instance, an aqueous solution of the pharmaceutical substance and an aqueous solution of albumin are mixed together in an appropriate proportion, and the resultant mixture is lyophized to make a solid mixture. Furthermore, for instance, the pharmaceutical substance in a solid state is suspended in an aqueous solution of albumin, followed by lyophilization to make a solid mixture.

Illustrating the preparation process more in detail, the matrix type preparation may be manufactured, for instance, by mixing uniformly a pharmaceutical substance or its mixture with albumin and an elastomer base optionally with a plasticizer (e.g. dimethylpolysiloxane ("Silastic 360")), adding a curing agent thereto and stirring the resultant mixture. The mixture is then filled in an appropriate mold, followed by curing at room temperature to give a shaped composition. In an alternative way, a core material not containing a pharmaceutical substance may be covered by a silicone elastomer containing a pharmaceutical substance or its mixture with albumin to make a shaped composition. As the core material, any non-toxic one may be used, but the use of an elastic polymer is preferred from the viewpoint of easy handling. When desired, stabilizers, preservatives, soothing agents, solubilizers, plasticizers, release controlling agents, etc. may be incorporated into the composition. There may be also incorporated other additives such as water-soluble or fat-soluble mixing agents as stated above.

The membrane permeation type preparation in which the pharmaceutical substance is contained in a hollow vessel made of the silicone elastomer and released through the wall of the vessel may be manufactured, for instance, by admixing an elastomer base optionally containing albumin with a curing agent and shaping the resultant mixture in an appropriate mold to obtain a hollow vessl having an optional shape. Into the hollow vessel, a pharmaceutical substance or its mixture with albumin in the form of solid, liquid, gel or the like is filled to give the objective preparation. If necessary, appropriate additives may be incorporated into the preparation at any stage.

The preparation of the sustained release composition as above manufactured may have any optional shape or form (e.g. globule, semi-globule, pillar, needle, tube, button, sheet, capsule, microcapsule), which is suitable for application. It is usually applied by subcutaneous administration, implantation into internal organs, insertion into body cavity or the like. When the preparation is formed in a pillar, needle or tube shape of not more than about 4 mm (preferably about 0.5 to 2 mm) in diameter and not more than about 50 mm (preferably about 5 to 30 mm) in length, it can be conveniently administered into a living body with no need of surgical operation. For instance, it may be injectionally administered into a living body by the use of an appropriate tool such as a fiber scope, a clamping needle or a tool as disclosed in Japanese Patent Publication (unexamined) No. 227,772/85 Particularly when the preparation is shaped to have a diameter of not more than 1.7 mm, it can be easily administered by the use of a conventional detention needle (14G).

The sustained release composition of the invention may be applied not only to human beings but also mammals such as cow, sheep, pigs, rabbits, chickens, fowls and birds. Depending upon the kind, bodyweight, age, etc. of the living body to be administered, the kind and dose of the pharmaceutical substance may be varied.

The following examples are presented for further illustration of the invention, and the part(s) and % therein are by weight.

Example 1

A lyophilized product of human growth hormone (HGH) (50 IU) was added to a silicone elastomer base ("Silastic 382") (1 g), and glycerol (100 mg) and sodium chloride (100 mq) were added thereto, followed by stirring. To the resultant mixture, stannous octate (5 mg) as a curing agent was added, followed by further stirring. The resulting mixture was injected into a polyethylene tube of 1.5 mm in inner diameter and cured for 5 hours. The cured silicone elastomer was taken off from the tube and cut in 10 mm long to obtain a matrix type sustained release preparation having an HGH content of 1.8 % by weight in a cylindrical form.

Example 2

A silicone elastomer base ("Dow Corning MDX-4-4210") (1 g) was admixed with finely pulverized sodium chloride (200 mg), followed by stirring. To the resultant mixture, chloroplatinic acid (100 mg) as a curing agent was added, followed by further stirring. The resulting mixture was defoamed by the aid of a vacuum pump and injected into a teflon tube of 3 mm in inner diameter, and a teflon tube of 2 mm in outer diameter was inserted into the center. After curing for 24 hours, the cured silicone elastomer was taken off from the tubes and cut in 30 mm long to obtain a silicone elastomer tube of 3 mm in outer diameter, 2 mm in inner diameter and 30 mm in length An aqueous solution of interferon alpha ($1 \times 10^6$ IU) (90 μl) was introduced into the silicone elastomer tube, which was then sealed with an adhesive agent (silicone type A) at both ends to obtain a membrane permeation type sustained release preparation having an interferon alpha content of $2 \times 10^{-3}$ % by weight.

Example 3

A silicone elastomer base ("Silastic 382") (300 mg) was admixed with glycerol (50 mg) and finely pulverized sodium chloride (75 mg), followed by stirring. To the resultant mixture, GRF(1-29)NH$_2$ (50 mg) and then stannous octate (2 mg) as a curing agent were added, followed by further stirring. The resulting mixture was injected into a teflon tube of 1.8 mm in inner diameter and cured for 24 hours. The cured silicone elastomer was cut in 9 mm long and taken off from the tube to obtain a matrix type sustained release preparation having a GRF content of 10.5 % by weight.

Example 4

A silicone elastomer base ("Silastic 382") (400 mg), and glycerol (50 mg) and sodium chloride (75 mg) were added thereto, followed by stirring. To the resultant mixture, GRF(1-29) (50 mg) and then stannous octate (4 mg) as a curing agent was added, followed by further stirring. The resulting mixture was injected into a teflon tube of 1.8 mm in inner diameter and cured for 24 hours. The cured silicone elastomer was cut in 9 mm long and taken off from the tube to obtain a matrix type sustained release preparation having a GRF content of 8.6 % by weight.

Test 1

The sustained release preparation as obtained in Example 3 was admitted in a physiological saline solution (3 ml) and shaken (30 Hz). The GRF(1-29)NH$_2$ released from said preparation was quantitatively determined by high performance liquid chromatography, and the accumulated release amount with time is indicated in FIG. 1 of the accompanying drawings. From this Figure, it is understood that the release behavior of GRF is good.

Test 2

Figure 2:
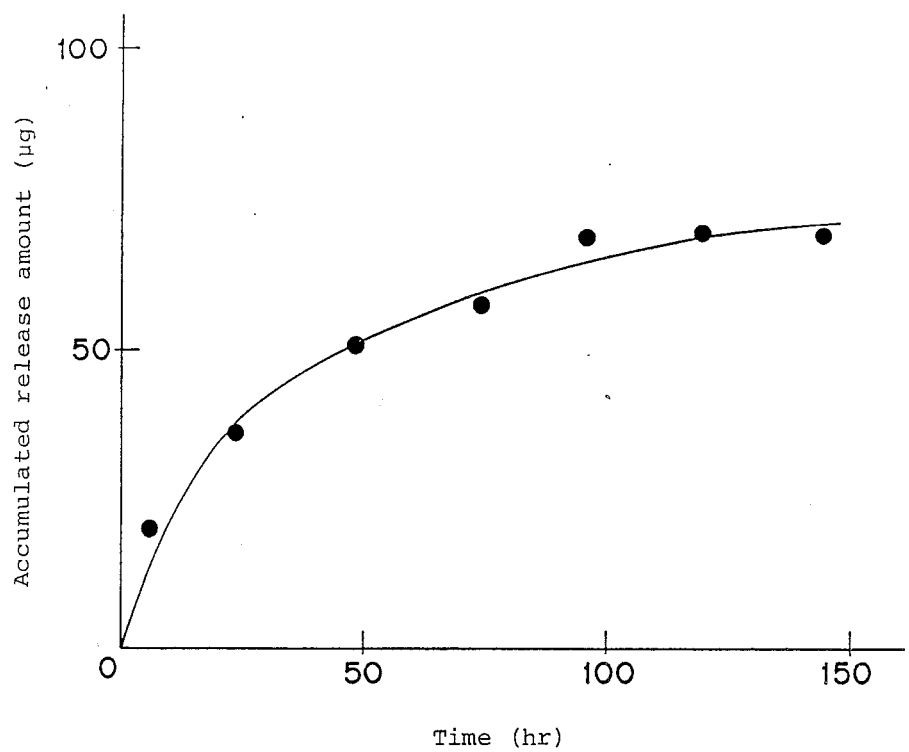

The sustained release preparation as obtained in Example 4 was admitted in a physiological saline solution (3 ml) and shaken (30 Hz). The GRF(1-29)NH$_2$ released from said preparation was quantitatively determined by high performance liquid chromatography, and the accumulated release amount with time is indicated in FIG. 2 of the accompanying drawings. From this Figure, it is understood that the release behavior of GRF is good.

Example 5

Sustained release preparation (I):

To a mixture of a silicone elastomer base ("Silastic 382") (0.75 g) and another silicone elastomer base ("Dow Corning 360") (0.75 g), human serum albumin (HSA) (642 mg) was added, followed by kneading. Then, stannous octate (110 mg) as a curing agent was added thereto, followed by further kneading. The resultant mixture was introduced into a polypropylene tube of 2.9 mm in inner diameter and allowed to stand at room temperature for 24 hours, whereby curing proceeded. The cured silicone elastomer was taken off from the polypropylene tube and cut in 25 mm long to give a matrix type sustained release preparation (I) in a cylindrical shape.

Sustained release preparation (II):

In the same manner as in the case of the sustained release preparation (I) but using a silicone elastomer base ("Silastic 382") (1.35 g), another silicone elastomer base ("Dow Corning 360") (0.15 g), HSA (642 mg) and stannous octate (110 mg), there was prepared a matrix type sustained release preparation (II) in a cylindrical shape (2.9 mm in diameter and 25 mm in length).

Sustained release preparation (III):

In the same manner as in the case of the sustained release preparation (I) but using a silicone elastomer base ("Silastic 382") (1.5 g), HSA (642 mg) and stannous octate (110 mg), there was prepared a matrix type sustained release preparation (III) in a cylindrical shape (2.9 mm in diameter and 25 mm in length).

Example 6

Sustained release preparation (IV) (for control):

To a mixture of a silicone elastomer base ("Silastic 382") (0.5 g) and another silicone elastomer base ("Dow Corning 360") (0.05 g), N-acetyltryptophan sodium (5 mg) was added, followed by kneading. Then, stannous octate (55 mg) as a curing agent was added thereto, followed by further kneading. The resultant mixture was introduced into a polypropylene tube of 4.8 mm in inner diameter and allowed to stand at room temperature for 24 hours, whereby curing proceeded. The cured silicone elastomer was taken off from the polypropylene tube and cut in 10 mm long to give a matrix type sustained release preparation (IV) in a cylindrical shape.

Sustained release preparation (V) (the invention):

To a mixture of a silicone elastomer base ("Silastic 382") (0.5 g) and another silicone elastomer base ("Dow Corning 360") (0.05 g), a lyophilized product of a solution of N-acetyltryptophan sodium (5 mg) in 25 % HSA solution (0.93 ml) was added, followed by kneading. Then, stannous octate (55 mg) as a curing agent was added thereto, followed by further kneading. The resultant mixture was introduced into a polypropylene tube of 4.8 mm in inner diameter and allowed to stand at room temperature for 24 hours, whereby curing proceeded. The cured silicone elastomer was taken off from the polypropylene tube and cut in 10 mm long to give a matrix type sustained release preparation (V) in a cylindrical shape.

Example 7

Sustained release preparation (VI) (for control):

A silicone elastomer base ("Silastic 382") (7.0 g) A silicone elastomer base ("Silastic 382") (7.0 g) and another silicone elastomer base ("Dow Corning 360") (0.7 g) were mixed together. To the resultant mixture (0.6 g), indomethacin (107 mg) and sodium chloride (192 mg) were added, followed by kneading. Then, stannous octate (60 mg) as a curing agent was added thereto, followed by further kneading. The resultant mixture was introduced into a polypropylene tube of 2.9 mm in inner diameter and allowed to stand at room temperature for 24 hours, whereby curing proceeded. The cured silicone elastomer was taken off from the polypropylene tube and cut in 13 mm long to give a matrix type sustained release preparation (VI) containing 30 mg of indomethacin in a cylindrical shape.

Sustained release preparation (VII) (the invention):

A silicone elastomer base ("Silastic 382") (7.0 g) and another silicone elastomer base ("Dow Corning 360") (0.7 g) were mixed together. To the resultant mixture (0.6 g), a lyophilized product of a solution of indomethacin (100 mg) in 25% HSA solution (0.8 ml) was added, followed by kneading. Then, stannous octate (60 mg) as a curing agent was added thereto, followed by further kneading. The resultant mixture was introduced into a polypropylene tube of 2.9 mm in inner diameter and allowed to stand at room temperature for 24 hours, whereby curing proceeded. The cured silicone elastomer was taken off from the polypropylene tube and cut in 12.5 mm long to give a matrix type sustained release preparation (VII) containing 30 mg of indomethacin in a cylindrical shape.

Sustained release preparation (VIII) (for control):

A silicone elastomer base ("Silastic 382") (7.0 g) and another silicone elastomer base ("Dow Corning 360") (0.7 g) were mixed together. To the resultant mixture (0.6 g), indomethacin (112 mg) was added, followed by kneading. Then, stannous octate (60 mg) as a curing agent was added thereto, followed by further kneading. The resultant mixture was introduced into a polypropylene tube of 2.9 mm in inner diameter and allowed to stand at room temperature for 24 hours, whereby curing proceeded. The cured silicone elastomer was taken off from the polypropylene tube and cut in 10 mm long to give a matrix type sustained release preparation (VIII) containing 30 mg of indomethacin in a cylindrical shape.

Example 8

Sustained release preparation (IX):

To a mixture of a silicone elastomer base ("Silastic 382") (1 g) and another silicone elastomer base ("Dow Corning 360") (0.1 g), a lyophilized product of a mixture of alpha-interferon ($2.6 \times 10^6$ IU/ml) (2.2 ml) and 25% HSA solution (2.2 ml) was added, followed by kneading. Then, stannous octate (166 mg) as a curing agent was added thereto, followed by further kneading. The resultant mixture was introduced into a polypropylene tube of 4.8 mm in inner diameter and allowed to stand at room temperature for 24 hours, whereby curing proceeded. The cured silicone elastomer was taken off from the polypropylene tube and cut in 12 mm long to give a matrix type sustained release preparation (IX) in a cylindrical shape.

Test 3

Figure 3:
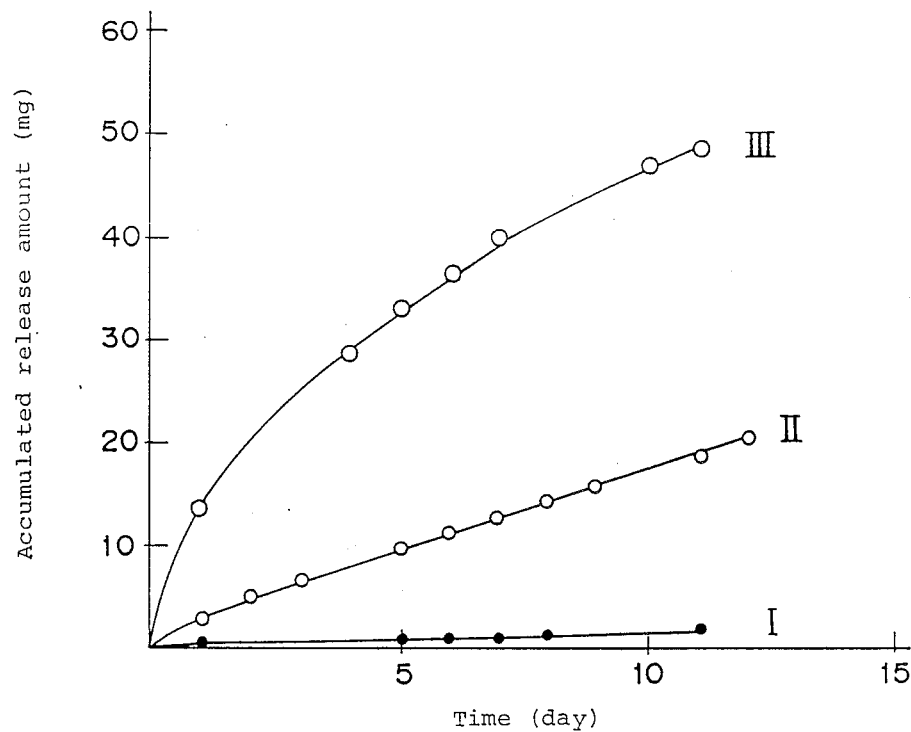

Each of the sustained release preparations (I), (II) and (III) as obtained in Example 5 was admitted in a physiological saline solution (20 ml) and shaken (amplitude, 4 cm; 60 reciprocation/minute) at 25° C. The HSA released from said preparation was quantitatively determined by measurement of absorbance at 280 nm, and the accumulated release amount with time is indicated in FIG. 3 of the accompanying drawings. From this Figure, it is understood that the release behavior of HSA is varied with the composition in the preparation.

Test 4

Figure 4:
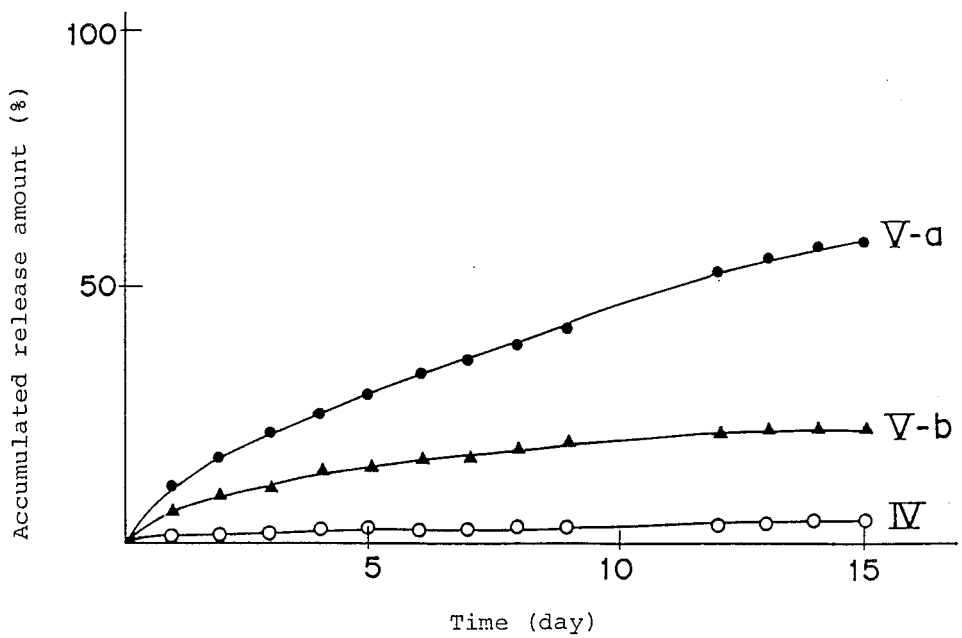

Each of the sustained release preparations (IV) and (V) as obtained in Example 6 was subjected to releasing test in the same manner as in Test 3. N-Acetyltryptophan sodium released from said preparation was quantitatively determined by measurement of absorbance in case of the preparation (IV) or by high performance liquid chromatography in case of the preparation (V). The accumulated release amount with time is indicated in FIG. 4 of the accompanying drawings wherein V-a is the curve on N-acetyltryptophan and V-b is HSA. From this Figure, it is understood that the release rate of N-acetyltryptophan sodium is increased significantly by addition of HSA thereto.

Test 5

Figure 5:
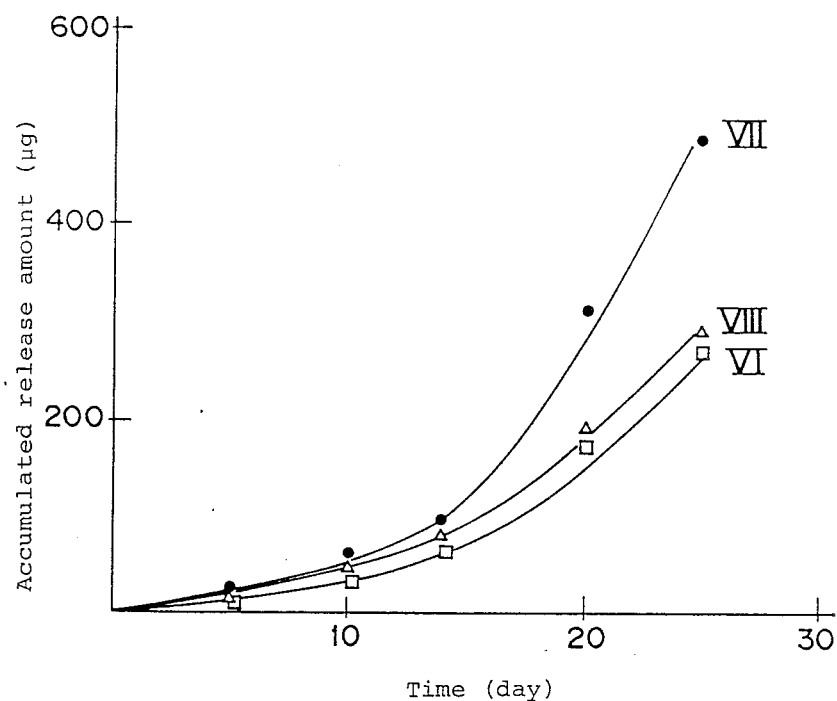

Each of the sustained release preparations (VI), (VII) and (VIII) as obtained in Example 7 was admitted in a physiological saline solution (10 ml) and shaken at 25° C. The indomethacin released from said preparation was quantitatively determined by high performance liquid chromatography, and the accumulated release amount with time is indicated in FIG. 5 of the accompanying drawings. From this Figure, it is understood that the release rate of indomethacin is increased significantly by addition of HSA thereto.

Test 6

Figure 6:
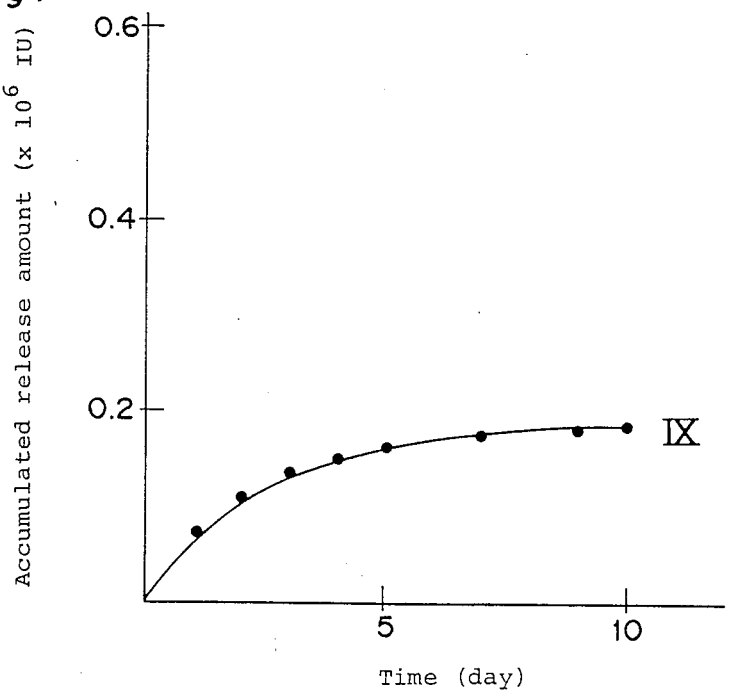

The sustained release preparation (IX) as obtained in Example 8 was admitted in a PBS buffer solution containing 0.5 % HSA (20 ml) and shaken at 25° C. The alpha-interferon released from said preparation was quantitatively determined by radio-imuno assay, and the accumulated release amount with time is indicated in FIG. 6 of the accompanying drawings. From this Figure, it is understood that alpha-interferon which is known to be an unstable protein showing its pharmaceutical effect in a trace amount can be stabilized and gives a pharmaceutically effective release by addition of HSA thereto.

We claim:

1. A sustained release composition comprising a silicone elastomer matrix, a pharmaceutical substance uniformly mixed in said matrix and albumin to provide sustained release of said pharmaceutical substance from said silicone elastomer matrix and stabilize said pharmaceutical substance in said silicone elastomer matrix.

2. A sustained release composition comprising a silicone elastomer matrix, a pharmaceutical substance dispersed in said matrix and albumin to provide sustained release of said pharmaceutical substance from said silicone elastomer matrix and stabilize said pharmaceutical substance in said silicone elastomer matrix.

3. A sustained release composition comprising a hollow vessel of a silicone elastomer matrix, having a pharmaceutical substance and albumin contained within said hollow vessel.

4. A sustained release composition comprising a silicone elastomer matrix, a pharmaceutical substance dispersed in said matrix in an amount of from 1 to 20% by weight and albumin in an amount of from 20 to 30% by weight to provide sustained release of said pharmaceutical substance from said silicone elastomer matrix and stabilize said pharmaceutical substance in said silicone elastomer matrix.

5. A method for enhancing the amount or concentration of a pharmaceutical substance as released from a sustained release composition comprising uniformly mixing a pharmaceutical substance with a silicone elastomer and albumin to provide sustained release of said pharmaceutical substance from said silicone elastomer matrix and stabilize said pharmaceutical substance in said silicone elastomer matrix.

6. A method according to claim 5, wherein said pharmaceutical substance is mixed in an amount of from 1 to 20% by weight and said albumin is mixed in an amount of from 20 to 30% by weight.

7. A sustained release composition comprising a silicone elastomer matrix, a pharmaceutical substance and albumin to provide sustained release of said pharmaceutical substance from said silicon elastomer matrix and stabilize said pharmaceutical substance in said silicon elastomer matrix.

8. The composition according to claim 1, wherein the pharmaceutical substance is contained in a context of not more than 15% by weight.

9. The composition according to claim 1 or 2, which is an injectable composition.

10. The composition according to claim 9, which is molded in a cylindrical, needle or tube shape.

11. The composition according to claim 10, which is shaped in a diameter of not more than 4 mm and a length of not more than 50 mm.

12. The composition according to claim 1 or 2, wherein the pharmaceutical substance has a molecular weight of 1,000 to 500,000.

13. The composition according to claim 1 or 2 wherein the pharmaceutical substance is one desired to be administered in a trace amount continuously over a long period of time.

14. The composition according to any of claims 1 to 3, wherein the pharmaceutical substance is a substance having growth regulating activity, a substance having bone metabolizing activity, a substance having thrombolytic activity or a substance having immumoregulating activity.

15. The composition according to any of claims 1 to 34, wherein the pharmaceutical substance is a substance having anti-inflammatory activity.

16. The composition according to any of claims 1 to 3, wherein the pharmaceutical substance is continuously released over a long period of time from the silicone elastomer as the matrix.

17. The composition according to any of claims 1 to 3, wherein the pharmaceutical substance is contained within a hollow vessel comprised of said silicone elastomer, whereby said pharmaceutical substance is continuously released over a long period of time through the wall of said hollow vessel.

18. The composition according to claim 1 or 2, wherein the pharmaceutical substance is contained in a content of not more than 50% by weight.

19. The composition according to claim 1 or 2, wherein the albumin is contained in a content of not more than 50% by weight.

20. The composition according to claim 1 or 2, wherein the pharmaceutical substance is contained in a content of not more than 50% by weight and the albumin is contained in a content of not more than 50% by weight.

21. The composition according to claim 14, wherein the pharmaceutical substance having growth regulating activity is growth hormone, growth hormone releasing factor or somatomedin.

22. The composition according to claim 14, wherein the pharmaceutical substance having bone metabolizing activity is calcitonin.

23. The composition according to claim 14, wherein the pharmaceutical substance having thrombolytic activity is tissue plasminogen activator.

24. The composition according to claim 14, wherein the pharmaceutical substance having immunoregulating activity is interferon, interleukin, colony stimulating factor, macrophage activating factor or macrophage migration inhibitory factor.

* * * * *